United States Patent

Bartmann et al.

Patent Number: 5,230,829
Date of Patent: Jul. 27, 1993

[54] PHENYLCYCLOHEXANES, AND A LIQUID-CRYSTALLINE MEDIUM

[75] Inventors: Ekkehard Bartmann, Erzhauzen; Joachim Krause, Dieburg; Eike Poetsch, Mühltal; Reinhard Hittich, Modautal, all of Fed. Rep. of Germany; Bernhard Rieger, Yokohama, Japan; Ulrich Finkenzeller, Plankstadt, Fed. Rep. of Germany

[73] Assignee: Merck Patent Gesellschaft mit beschrankter Haftung, Darmstadt, Fed. Rep. of Germany

[21] Appl. No.: 679,078

[22] Filed: Jun. 24, 1991

[30] Foreign Application Priority Data

Apr. 21, 1990 [DE] Fed. Rep. of Germany ....... 4012764

[51] Int. Cl.$^5$ ..................... C09K 19/30; C09K 19/52; C09K 19/12
[52] U.S. Cl. .................... 252/299.63; 252/299.01; 252/299.66
[58] Field of Search ............. 252/299.01, 299.61, 252/299.63, 299.66

[56] References Cited

U.S. PATENT DOCUMENTS 4,846,998 11/1989 Pohl et al. ................. 252/299.63

FOREIGN PATENT DOCUMENTS 3732284 4/1989 Fed. Rep. of Germany .
3807872 9/1989 Fed. Rep. of Germany .
3909802 4/1990 Fed. Rep. of Germany .

Primary Examiner—Robert L. Stoll
Assistant Examiner—Shean C. Wu
Attorney, Agent, or Firm—Millen, White, Zelano & Branigan

[57] ABSTRACT

The invention relates to novel phenylcyclohexanes of the formula I in which
Q is CH—Hal or C—Hal$_2$ where Hal is F or Cl,
n is 1 to 5,
r is 0 to 6,
A is a single bond, X is F, Cl, —CF$_3$, —OCF$_3$ or —OCHF$_2$, and
Y and Z are each, independently of one another, H or F.

13 Claims, No Drawings

PHENYLCYCLOHEXANES, AND A LIQUID-CRYSTALLINE MEDIUM

SUMMARY OF THE INVENTION

The invention relates to novel phenylcyclohexanes of the formula I

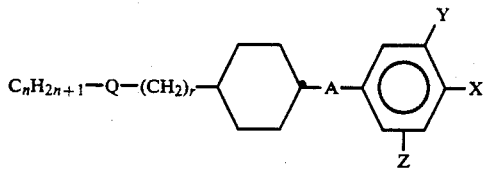

in which
Q is CH—Hal or C—Hal$_2$ where Hal is F or Cl,
n is 1 to 5,
r is 0 to 6,
A is a single bond,

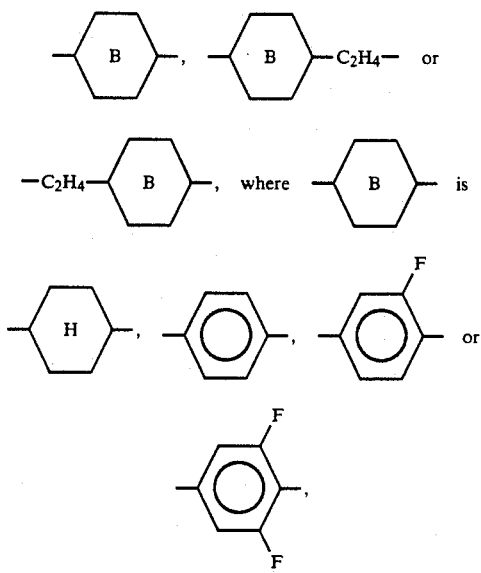

X is F, Cl, —CF$_3$, —OCF$_3$ or —OCHF$_2$, and
Y and Z are each, independently of one another, H or F.

DE-A No. 33 32 692 mentions the liquid-crystal compounds mentioned below:
4-(2-fluorobutyl)-4'-cyanobiphenyl
4-(1-fluoropentyl)-4'-cyanobiphenyl
4-(2-fluoropentyl)-4'-cyanobiphenyl
4-(3-fluoropentyl)-4'-cyanobiphenyl
4-(1-fluoropentyl)-4''-cyano-p-terphenyl
4-(2-fluoropropyl)-4''-cyano-p-terphenyl
1-(4-trans-(1-fluoropentyl)cyclohexyl)-4-cyanobenzene
1-(4-trans-(2-fluoropentyl)cyclohexyl)-4-cyanobenzene
1-(4-trans-(3-fluoropentyl)cyclohexyl)-4-cyanobenzene However, the compounds described therein carry, on the one hand, only one halogen atom in the terminal group and, on the other hand, nitrile groups and are liquid crystals of very positive dielectric anistropy. Compounds of this type are not up to the high demands regarding electrical resistance, as are required, for example, for displays having an active matrix.

Like similar compounds, for example those known from DE-A No. 26 36 684, the compounds of the formula I can be used as components of liquid-crystalline media, in particular for displays based on the principle of the twisted cell.

The substances employed hitherto for this purpose all have certain disadvantages, for example excessively high melting points, excessively low clearing points, inadequate stability to the action of light heat, or electrical fields, inadequate electrical resistance, unfavorable elastic properties or excessive temperature dependence of the threshold voltage.

In particular in displays of the supertwist type (STN) having twist angles of significantly greater than 220° C. or in displays having an active matrix, the materials employed hitherto have disadvantages.

The invention had the object of finding novel liquid-crystalline compounds which are suitable as components of liquid-crystalline media, in particular for nematic media having positive dielectric anistropy, and which do not have the disadvantages of the known compounds, or only do so to a lesser extent. This object has been achieved by the provision of the novel compounds of the formula I.

It has been found that the compounds of the formula I are eminently suitable as components of liquid-crystalline media. In particular, they can be used to obtain liquid-crystalline media having broad nematic ranges, excellent nematogeneity down to low temperatures, excellent chemical stability, excellent elastic properties, pronounced $\epsilon\perp$ at positive dielectric anistropy, low temperature dependence of the threshold voltage and-/or low optical anistropy.

In addition, the novel compounds have good solubility for other components of media of this type and high positive dielectric anistropy at the same time as favorable viscosity.

The compounds of the formula I make it possible to produce both STN displays having a very steep electro-optical characteristic line and displays having an active matrix with excellent long-term stability. A suitable choice of r and n allows the threshold voltages in both types of display to be significantly reduced.

In the pure state, the compounds of the formula I are colorless and form liquid-crystalline mesophases in a temperature range which is favorably located for electrooptical use.

The invention thus relates to the compounds of the formula I and to the use of the compounds of the formula I as components of liquid-crystalline media, to liquid-crystalline media containing at least one compound of the formula I, and to electrooptical displays which contain media of this type.

Above and below, r, n, A, X, Y and Z are as defined above, unless expressly stated otherwise.

In the compounds of the formula I, the alkylene groups (CH$_2$), are preferably straight-chain. Accordingly, they are preferably a single bond (r=0), methylene, ethylene, n-propylene, n-butylene, n-pentylene or n-hexylene. r is preferably 2 or 4, furthermore preferably 3 or 5. $C_nH_{2n+1}$ is a preferably straight-chain alkyl radical, preferably having up to 3 carbon atoms.

The radical is preferably

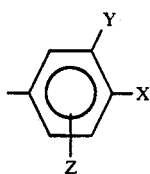

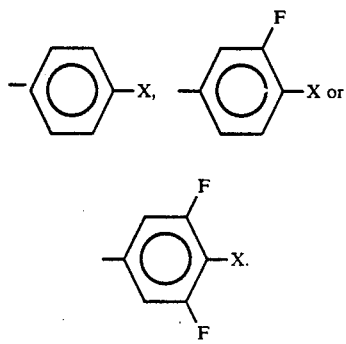

X is preferably F, Cl, —CF$_3$ or —OCF$_3$.

In addition, the compounds of the formula I can be prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for the reactions mentioned. Use may also be made here of variants which are known per se, but are not described here in greater detail.

If desired, the starting materials can also be formed in situ by not isolating them from the reaction mixture, but instead immediately reacting them further to give the compounds of the formula I.

Precursors which are suitable for the synthesis of the compounds according to the invention can be obtained, for example, in accordance with the following synthesis schemes:

Scheme 1:

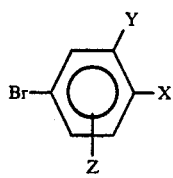

1. BuLi/−70°
2. TiCl(OiPr)$_3$/THF

3. ROOC—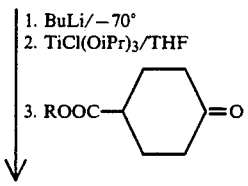=O

-continued
Scheme 1:

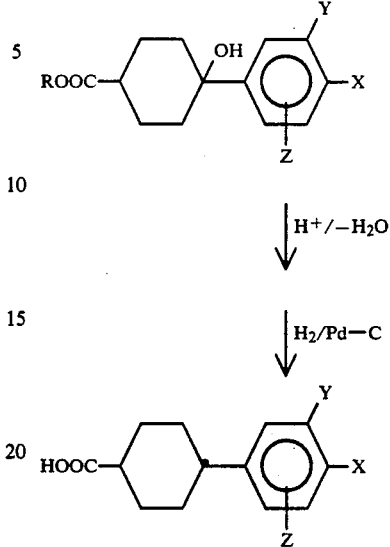

The Grignard compound obtained from the corresponding bromobenzene derivative is reacted with chlorotrialkyl orthotitanate or -zirconate by the method of WO 87/05599 to give the tertiary cyclohexanol. Elimination of water, hydrogenation of the double bond and isomerization give, by conventional methods, the transcyclohexanecarboxylic acid.

Some of the bromobenzene derivatives used as starting materials are known, and some can be prepared without difficulties from compounds known from the literature by standard methods of organic chemistry. For example, the OCF$_3$ or OCHF$_2$ compounds are obtainable by known methods from the corresponding phenols and the CF$_3$ or CN compounds are obtainable from the corresponding benzoic acids. Compounds of the formula

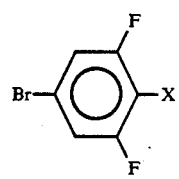

or corresponding monofluorinated compounds can be obtained, for example, from the known precursors where X =H by lithiation at low temperatures and subsequent reaction with a suitable electrophile.

The corresponding cyclohexanecarboxylic acids in which A is 1,4-phenylene, 3,5-difluoro-1,4-phenylene or 3-fluoro-1,4-phenylene can be prepared analogously to the above synthesis schemes, with the X,Y,Z-substituted bromobenzene being replaced by a compound

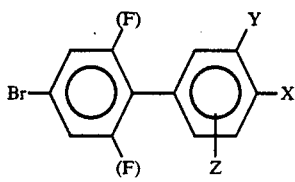

which can be prepared by noble metal-catalyzed coupling reactions (E. Poetsch, Kontakte (Darmstadt) 1988 (2), p. 15).

The scheme below gives a synthesis of the precursors which are suitable for the preparation of the compounds where A=trans-1,4-cyclohexylene:

Scheme 2:

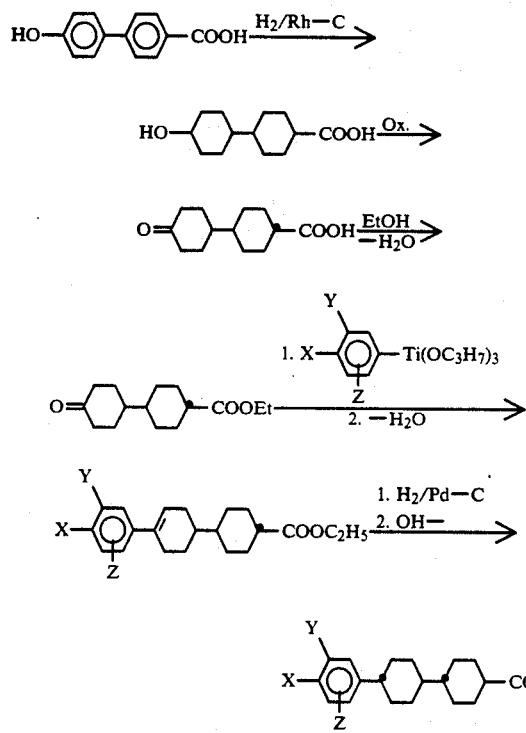

The higher homologs of the cyclohexanecarboxylic acids (r=1 to 6) can be obtained by routine methods from the cyclohexanecarboxylic acids described above (r=0):

Scheme 3:

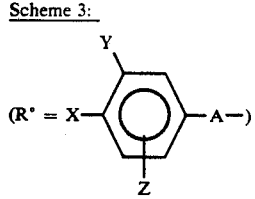

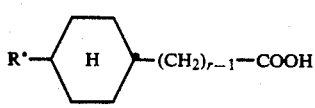

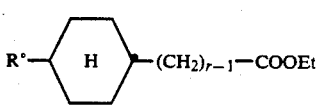

↓ Vitride

Scheme 3:

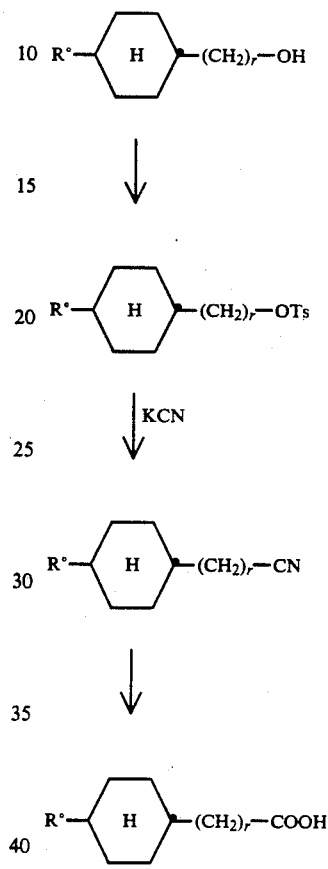

The higher homologs can be obtained by repeating this reaction sequence analogously.

The homologization indicated in the above reaction scheme can also be carried out be other standard methods known to a person skilled in the art.

The carboxylic acids described above are convered into ketones or alcohols only in accordance with scheme 4, and the compounds of the formula I are obtained from the latter by routine halogenation reaction methods (for example $PCl_5$, $SF_4$, DAST):

Scheme 4:

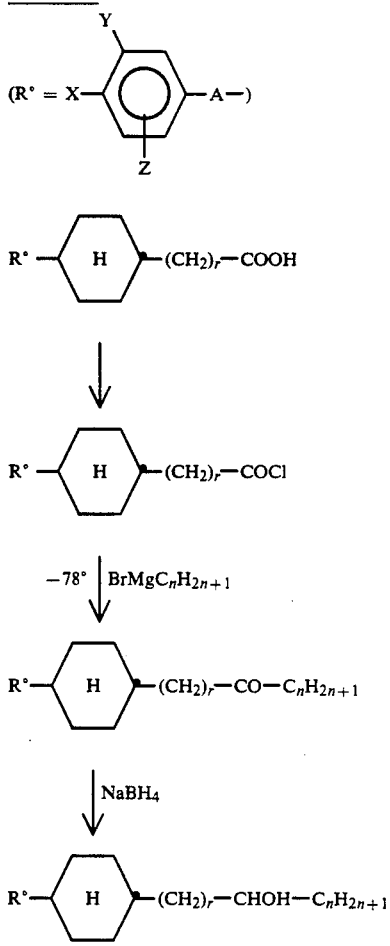

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylicacid,phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes and tolans.

The 1,4-phenylene groups in these compounds may also be fluorinated.

The most important compounds suitable as further constituents of media according to the invention can be characterized by the formulae 1, 2, 3, 4 and 5:

$$R'—L—E—R''  \quad 1$$

$$R'—L—COO—E—R''  \quad 2$$

$$R'—L—OOC—E—R''  \quad 3$$

$$R'—L—CH_2CH_2—E—R''  \quad 4$$

$$R'—L≡C—E—R  \quad 5$$

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorinesubstituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group comprising —Phe—Cyc—, —Cyc—Cyc—, —G—Phe— and —G—Cyc—.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —CF$_3$, —OCF$_3$, F, Cl or —NCS; in this case, R has the meaning given for the compounds of the sub-formulae 1a to 5a and is preferably alkyl or alkenyl. R" is preferably selected from the group comprising —F, Cl, CF$_3$ and —OCF$_3$. However, other variants of the proposed substituents in the compounds of the formulae 1, 2, 3, 4 and 5 are also common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention preferably also contain components from the group comprising the compounds 1b, 2b, 3b, 4b and 5b (Group 2), whose proportions are preferably as follows:

Group 1: 20 to 90%, in particular 30 to 90%,

Group 2: 10 to 80%, in particular 10 to 50%, the sum of the proportions of the compounds according to the invention and of the compounds from Groups 1 and 2 adding up to 100%.

The media according to the invention preferably contain 1% to 40%, in particular preferably 5% to 30%, of compounds according to the invention. Further preferred media are those which contain more than 40%, in particular 45% to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

EXAMPLES

The examples below are intended to illustrate the invention without representing a limitation. mp.=melting point, cp.=clearing point. Above and below, percentages are percent by weight; all temperatures are indicated in degrees Celsius. "Customary work-up" means that water is added, the mixture is extracted with methylene chloride, and the organic phase is separated off, dried and evaporated, and the product is purified by crystallization and/or chromatography.

In addition, the abbreviations have the following meanings:

C: crystalline-solid state, S: smectic phase (the index characterizes the phase type), N: nematic state, Ch: cholesteric phase, I: isotropic phase. The number between two symbols indicates the conversion temperature in degrees Celsius.

| DAST | diethylaminosulfur trifluoride |
|---|---|
| DCC | dicyclohexylcarbodiimide |
| DDQ | dichlorodicyanobenzoquinone |
| DIBALH | diisobutylaluminum hydride |
| DMSO | dimethyl sulfoxide |
| POT | potassium tertiary-butanolate |
| THF | tetrahydrofuran |
| pTSOH | p-toluenesulfonic acid |

EXAMPLE 1

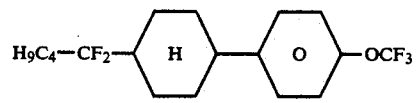

12.5 g of 4-(trans-4-valeroylcyclohexyl)-1-trifluoromethoxybenzene (prepared from trans-4-(4-trifluoromethoxyphenyl)cyclohexanecarboxylic acid by conversion into the corresponding nitrile and subsequent reaction with butylmagnesium bromide) and 10 ml of diethylaminosulfur trifluoride (DAST) are slowly warmed to 85° with stirring. The mixture is allowed to react at this temperature for three hours, a further 5 ml of DAST are added, and the mixture is stirred at 85° for a further 18 hours.

After cooling, the mixture is diluted with dichloromethane and carefully hydrolyzed using water with ice cooling. The organic phase is separated off and washed with sodium bicarbonate [sic] solution and water until neutral, and the solvent is removed by distillation. Chromatographic purification gives 6.5 g of 4[trans-4-(1,1-difluoropentyl)cyclohexyl]trifluoromethoxybenzene.

EXAMPLE 2

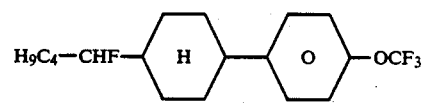

0.2 mol of DAST is added to a solution of trans-1-p-trifluoromethoxyphenyl-4-(1-hydroxypentyl)cyclohexane [prepared in accordance with scheme 4] in 150 ml of methylene chloride, and the mixture is processed further as described in Example 1, giving trans-1-p-trifluoro-methoxyphenyl-4-(1-fluoropentyl)cyclohexane.

EXAMPLE 3

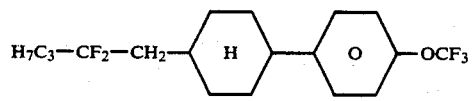

4-[trans-4-(2,2-Difluoropentyl)cyclohexyl]trifluoromethoxybenzene is obtained analogously from 1-[trans-4-(4-trifluoromehoxyphenyl)cyclohexyl]pentan-2-one (prepared from trans-4-(4-trifluoromethoxyphenyl)cyclohexanecarboxylic acid by reduction using lithium aluminum hydride to give the carbinol, conversion into the tosylate, reaction thereof with sodium cyanide to give the nitrile and subsequent Grignard reaction with propylmagnesium bromide).

EXAMPLES 4

| | | (A = a single bond, '—') | | | | |
|---|---|---|---|---|---|---|
| n | r | Q | X | Y | Z | A |
| 1 | 1 | $CF_2$ | $OCF_3$ | H | H | '—' |
| 2 | 1 | $CF_2$ | $OCF_3$ | H | H | '—' |
| 3 | 1 | $CF_2$ | $OCF_3$ | H | H | '—' |
| 5 | 1 | $CF_2$ | $OCF_3$ | H | H | '—' |
| 1 | 1 | CHF | $OCF_3$ | H | H | '—' |
| 2 | 1 | CHF | $OCF_3$ | H | H | '—' |
| 3 | 1 | CHF | $OCF_3$ | H | H | '—' |
| 5 | 1 | CHF | $OCF_3$ | H | H | '—' |
| 1 | 2 | $CF_2$ | $OCF_3$ | H | H | '—' |
| 2 | 2 | $CF_2$ | $OCF_3$ | H | H | '—' |
| 4 | 2 | $CF_2$ | $OCF_3$ | H | H | '—' |
| 1 | 2 | CHF | $OCF_3$ | H | H | '—' |
| 2 | 2 | CHF | $OCF_3$ | H | H | '—' |
| 4 | 2 | CHF | $OCF_3$ | H | H | '—' |
| 1 | 3 | $CF_2$ | $OCF_3$ | H | H | '—' |
| 3 | 3 | $CF_2$ | $OCF_3$ | H | H | '—' |
| 1 | 3 | CHF | $OCF_3$ | H | H | '—' |
| 3 | 3 | CHF | $OCF_3$ | H | H | '—' |
| 1 | 1 | $CF_2$ | $OCF_2H$ | H | H | '—' |
| 2 | 1 | $CF_2$ | $OCF_2H$ | H | H | '—' |
| 3 | 1 | $CF_2$ | $OCF_2H$ | H | H | '—' |
| 5 | 1 | $CF_2$ | $OCF_2H$ | H | H | '—' |
| 1 | 1 | CHF | $OCF_2H$ | H | H | '—' |

-continued

| | | (A = a single bond, '—') | | | | |
|---|---|---|---|---|---|---|
| n | r | Q | X | Y | Z | A |
| 2 | 1 | CHF | $OCF_2H$ | H | H | '—' |
| 3 | 1 | CHF | $OCF_2H$ | H | H | '—' |
| 5 | 1 | CHF | $OCF_2H$ | H | H | '—' |
| 1 | 2 | $CF_2$ | $OCF_2H$ | H | H | '—' |
| 2 | 2 | $CF_2$ | $OCF_2H$ | H | H | '—' |
| 4 | 2 | $CF_2$ | $OCF_2H$ | H | H | '—' |
| 1 | 2 | CHF | $OCF_2H$ | H | H | '—' |
| 2 | 2 | CHF | $OCF_2H$ | H | H | '—' |
| 4 | 2 | CHF | $OCF_2H$ | H | H | '—' |
| 1 | 3 | $CF_2$ | $OCF_2H$ | H | H | '—' |
| 3 | 3 | $CF_2$ | $OCF_2H$ | H | H | '—' |
| 1 | 3 | CHF | $OCF_2H$ | H | H | '—' |
| 3 | 3 | CHF | $OCF_2H$ | H | H | '—' |
| 1 | 1 | $CF_2$ | $OCF_2H$ | F | H | '—' |
| 2 | 1 | $CF_2$ | $OCF_2H$ | F | H | '—' |
| 3 | 1 | $CF_2$ | $OCF_2H$ | F | H | '—' |
| 5 | 1 | $CF_2$ | $OCF_2H$ | F | H | '—' |
| 1 | 1 | CHF | $OCF_2H$ | F | H | '—' |
| 2 | 1 | CHF | $OCF_2H$ | F | H | '—' |
| 3 | 1 | CHF | $OCF_2H$ | F | H | '—' |
| 5 | 1 | CHF | $OCF_2H$ | F | H | '—' |
| 1 | 2 | $CF_2$ | $OCF_2H$ | F | H | '—' |
| 2 | 2 | $CF_2$ | $OCF_2H$ | F | H | '—' |
| 4 | 2 | $CF_2$ | $OCF_2H$ | F | H | '—' |
| 1 | 2 | CHF | $OCF_2H$ | F | H | '—' |
| 2 | 2 | CHF | $OCF_2H$ | F | H | '—' |
| 4 | 2 | CHF | $OCF_2H$ | F | H | '—' |
| 1 | 3 | $CF_2$ | $OCF_2H$ | F | H | '—' |
| 3 | 3 | $CF_2$ | $OCF_2H$ | F | H | '—' |
| 1 | 3 | CHF | $OCF_2H$ | F | H | '—' |
| 3 | 3 | CHF | $OCF_2H$ | F | H | '—' |
| 1 | 1 | $CF_2$ | Cl | H | H | '—' |
| 2 | 1 | $CF_2$ | Cl | H | H | '—' |
| 3 | 1 | $CF_2$ | Cl | H | H | '—' |
| 5 | 1 | $CF_2$ | Cl | H | H | '—' |
| 1 | 1 | CHF | Cl | H | H | '—' |
| 2 | 1 | CHF | Cl | H | H | '—' |
| 3 | 1 | CHF | Cl | H | H | '—' |
| 5 | 1 | CHF | Cl | H | H | '—' |
| 1 | 2 | $CF_2$ | Cl | H | H | '—' |
| 2 | 2 | $CF_2$ | Cl | H | H | '—' |
| 4 | 2 | $CF_2$ | Cl | H | H | '—' |
| 1 | 2 | CHF | Cl | H | H | '—' |
| 2 | 2 | CHF | Cl | H | H | '—' |
| 4 | 2 | CHF | Cl | H | H | '—' |
| 1 | 3 | $CF_2$ | Cl | H | H | '—' |
| 3 | 3 | $CF_2$ | Cl | H | H | '—' |
| 1 | 3 | CHF | Cl | H | H | '—' |
| 3 | 3 | CHF | Cl | H | H | '—' |
| 1 | 1 | $CF_2$ | F | H | H | '—' |
| 2 | 1 | $CF_2$ | F | H | H | '—' |
| 3 | 1 | $CF_2$ | F | H | H | '—' |
| 5 | 1 | $CF_2$ | F | H | H | '—' |
| 1 | 1 | CHF | F | H | H | '—' |
| 2 | 1 | CHF | F | H | H | '—' |
| 3 | 1 | CHF | F | H | H | '—' |
| 5 | 1 | CHF | F | H | H | '—' |
| 1 | 2 | $CF_2$ | F | H | H | '—' |
| 2 | 2 | $CF_2$ | F | H | H | '—' |
| 4 | 2 | $CF_2$ | F | H | H | '—' |
| 1 | 2 | CHF | F | H | H | '—' |
| 2 | 2 | CHF | F | H | H | '—' |
| 4 | 2 | CHF | F | H | H | '—' |
| 1 | 3 | $CF_2$ | F | H | H | '—' |
| 3 | 3 | $CF_2$ | F | H | H | '—' |
| 1 | 3 | CHF | F | H | H | '—' |
| 3 | 3 | CHF | F | H | H | '—' |
| 1 | 1 | $CF_2$ | F | F | H | '—' |
| 2 | 1 | $CF_2$ | F | F | H | '—' |
| 3 | 1 | $CF_2$ | F | F | H | '—' |
| 5 | 1 | $CF_2$ | F | F | H | '—' |
| 1 | 1 | CHF | F | F | H | '—' |
| 2 | 1 | CHF | F | F | H | '—' |
| 3 | 1 | CHF | F | F | H | '—' |
| 5 | 1 | CHF | F | F | H | '—' |
| 1 | 2 | $CF_2$ | F | F | H | '—' |
| 2 | 2 | $CF_2$ | F | F | H | '—' |
| 4 | 2 | $CF_2$ | F | F | H | '—' |
| 1 | 2 | CHF | F | F | H | '—' |

-continued

| | | (A = a single bond, '—') | | | | |
|---|---|---|---|---|---|---|
| n | r | Q | X | Y | Z | A |
| 2 | 2 | CHF | F | F | H | '—' |
| 4 | 2 | CHF | F | F | H | '—' |
| 1 | 3 | $CF_2$ | F | F | H | '—' |
| 3 | 3 | $CF_2$ | F | F | H | '—' |
| 1 | 3 | CHF | F | F | H | '—' |
| 3 | 3 | CHF | F | F | H | '—' |
| 1 | 1 | $CF_2$ | Cl | F | H | '—' |
| 2 | 1 | $CF_2$ | Cl | F | H | '—' |
| 3 | 1 | $CF_2$ | Cl | F | H | '—' |
| 5 | 1 | $CF_2$ | Cl | F | H | '—' |
| 1 | 1 | CHF | Cl | F | H | '—' |
| 2 | 1 | CHF | Cl | F | H | '—' |
| 3 | 1 | CHF | Cl | F | H | '—' |
| 5 | 1 | CHF | Cl | F | H | '—' |
| 1 | 2 | $CF_2$ | Cl | F | H | '—' |
| 2 | 2 | $CF_2$ | Cl | F | H | '—' |
| 4 | 2 | $CF_2$ | Cl | F | H | '—' |
| 1 | 2 | CHF | Cl | F | H | '—' |
| 2 | 2 | CHF | Cl | F | H | '—' |
| 4 | 2 | CHF | Cl | F | H | '—' |
| 1 | 3 | $CF_2$ | Cl | F | H | '—' |
| 3 | 3 | $CF_2$ | Cl | F | H | '—' |
| 1 | 3 | CHF | Cl | F | H | '—' |
| 3 | 3 | CHF | Cl | F | H | '—' |
| 1 | 1 | $CF_2$ | $OCF_3$ | H | H | Cyc |
| 2 | 1 | $CF_2$ | $OCF_3$ | H | H | Cyc |
| 3 | 1 | $CF_2$ | $OCF_3$ | H | H | Cyc |
| 5 | 1 | $CF_2$ | $OCF_3$ | H | H | Cyc |
| 1 | 1 | CHF | $OCF_3$ | H | H | Cyc |
| 2 | 1 | CHF | $OCF_3$ | H | H | Cyc |
| 3 | 1 | CHF | $OCF_3$ | H | H | Cyc |
| 5 | 1 | CHF | $OCF_3$ | H | H | Cyc |
| 1 | 2 | $CF_2$ | $OCF_3$ | H | H | Cyc |
| 2 | 2 | $CF_2$ | $OCF_3$ | H | H | Cyc |
| 4 | 2 | $CF_2$ | $OCF_3$ | H | H | Cyc |
| 1 | 2 | CHF | $OCF_3$ | H | H | Cyc |
| 2 | 2 | CHF | $OCF_3$ | H | H | Cyc |
| 4 | 2 | CHF | $OCF_3$ | H | H | Cyc |
| 1 | 3 | $CF_2$ | $OCF_3$ | H | H | Cyc |
| 3 | 3 | $CF_2$ | $OCF_3$ | H | H | Cyc |
| 1 | 3 | CHF | $OCF_3$ | H | H | Cyc |
| 3 | 3 | CHF | $OCF_3$ | H | H | Cyc |
| 1 | 1 | $CF_2$ | $OCF_2H$ | F | H | Cyc |
| 2 | 1 | $CF_2$ | $OCF_2H$ | F | H | Cyc |
| 3 | 1 | $CF_2$ | $OCF_2H$ | F | H | Cyc |
| 5 | 1 | $CF_2$ | $OCF_2H$ | F | H | Cyc |
| 1 | 1 | CHF | $OCF_2H$ | F | H | Cyc |
| 2 | 1 | CHF | $OCF_2H$ | F | H | Cyc |
| 3 | 1 | CHF | $OCF_2H$ | F | H | Cyc |
| 5 | 1 | CHF | $OCF_2H$ | F | H | Cyc |
| 1 | 2 | $CF_2$ | $OCF_2H$ | F | H | Cyc |
| 2 | 2 | $CF_2$ | $OCF_2H$ | F | H | Cyc |
| 4 | 2 | $CF_2$ | $OCF_2H$ | F | H | Cyc |
| 1 | 2 | CHF | $OCF_2H$ | F | H | Cyc |
| 2 | 2 | CHF | $OCF_2H$ | F | H | Cyc |
| 4 | 2 | CHF | $OCF_2H$ | F | H | Cyc |
| 1 | 3 | $CF_2$ | $OCF_2H$ | F | H | Cyc |
| 3 | 3 | $CF_2$ | $OCF_2H$ | F | H | Cyc |
| 1 | 3 | CHF | $OCF_2H$ | F | H | Cyc |
| 3 | 3 | CHF | $OCF_2H$ | F | H | Cyc |
| 1 | 1 | $CF_2$ | F | F | H | Cyc |
| 2 | 1 | $CF_2$ | F | F | H | Cyc |
| 3 | 1 | $CF_2$ | F | F | H | Cyc |
| 5 | 1 | $CF_2$ | F | F | H | Cyc |
| 1 | 1 | CHF | F | F | H | Cyc |
| 2 | 1 | CHF | F | F | H | Cyc |
| 3 | 1 | CHF | F | F | H | Cyc |
| 5 | 1 | CHF | F | F | H | Cyc |
| 1 | 2 | $CF_2$ | F | F | H | Cyc |
| 2 | 2 | $CF_2$ | F | F | H | Cyc |
| 4 | 2 | $CF_2$ | F | F | H | Cyc |
| 1 | 2 | CHF | F | F | H | Cyc |
| 2 | 2 | CHF | F | F | H | Cyc |
| 4 | 2 | CHF | F | F | H | Cyc |
| 1 | 3 | $CF_2$ | F | F | H | Cyc |
| 3 | 3 | $CF_2$ | F | F | H | Cyc |
| 1 | 3 | CHF | F | F | H | Cyc |
| 3 | 3 | CHF | F | F | H | Cyc |
| 1 | 1 | $CF_2$ | Cl | F | H | Cyc |

-continued (A = a single bond, '—')

| n | r | Q | X | Y | Z | A |
|---|---|---|---|---|---|---|
| 2 | 1 | $CF_2$ | Cl | F | H | Cyc |
| 3 | 1 | $CF_2$ | Cl | F | H | Cyc |
| 5 | 1 | $CF_2$ | Cl | F | H | Cyc |
| 1 | 1 | CHF | Cl | F | H | Cyc |
| 2 | 1 | CHF | Cl | F | H | Cyc |
| 3 | 1 | CHF | Cl | F | H | Cyc |
| 5 | 1 | CHF | Cl | F | H | Cyc |
| 1 | 2 | $CF_2$ | Cl | F | H | Cyc |
| 2 | 2 | $CF_2$ | Cl | F | H | Cyc |
| 4 | 2 | $CF_2$ | Cl | F | H | Cyc |
| 1 | 2 | CHF | Cl | F | H | Cyc |
| 2 | 2 | CHF | Cl | F | H | Cyc |
| 4 | 2 | CHF | Cl | F | H | Cyc |
| 1 | 3 | $CF_2$ | Cl | F | H | Cyc |
| 3 | 3 | $CF_2$ | Cl | F | H | Cyc |
| 1 | 3 | CHF | Cl | F | H | Cyc |
| 3 | 3 | CHF | Cl | F | H | Cyc |
| 1 | 1 | $CF_2$ | $OCF_2H$ | H | H | Phe |
| 2 | 1 | $CF_2$ | $OCF_2H$ | H | H | Phe |
| 3 | 1 | $CF_2$ | $OCF_2H$ | H | H | Phe |
| 5 | 1 | $CF_2$ | $OCF_2H$ | H | H | Phe |
| 1 | 1 | CHF | $OCF_2H$ | H | H | Phe |
| 2 | 1 | CHF | $OCF_2H$ | H | H | Phe |
| 3 | 1 | CHF | $OCF_2H$ | H | H | Phe |
| 5 | 1 | CHF | $OCF_2H$ | H | H | Phe |
| 1 | 2 | $CF_2$ | $OCF_2H$ | H | H | Phe |
| 2 | 2 | $CF_2$ | $OCF_2H$ | H | H | Phe |
| 4 | 2 | $CF_2$ | $OCF_2H$ | H | H | Phe |
| 1 | 2 | CHF | $OCF_2H$ | H | H | Phe |
| 2 | 2 | $CF_2$ | $OCF_2H$ | H | H | Phe |
| 4 | 2 | $CF_2$ | $OCF_2H$ | H | H | Phe |
| 1 | 3 | $CF_2$ | $OCF_2H$ | H | H | Phe |
| 3 | 3 | $CF_2$ | $OCF_2H$ | H | H | Phe |
| 1 | 3 | CHF | $OCF_2H$ | H | H | Phe |
| 3 | 3 | CHF | $OCF_2H$ | H | H | Phe |
| 1 | 1 | $CF_2$ | Cl | H | H | Phe |
| 2 | 1 | $CF_2$ | Cl | H | H | Phe |
| 3 | 1 | $CF_2$ | Cl | H | H | Phe |
| 5 | 1 | $CF_2$ | Cl | H | H | Phe |
| 1 | 1 | CHF | Cl | H | H | Phe |
| 2 | 1 | CHF | Cl | H | H | Phe |
| 3 | 1 | CHF | Cl | H | H | Phe |
| 5 | 1 | CHF | Cl | H | H | Phe |
| 1 | 2 | $CF_2$ | Cl | H | H | Phe |
| 2 | 2 | $CF_2$ | Cl | H | H | Phe |
| 4 | 2 | $CF_2$ | Cl | H | H | Phe |
| 1 | 2 | CHF | Cl | H | H | Phe |
| 2 | 2 | CHF | Cl | H | H | Phe |
| 4 | 2 | CHF | Cl | H | H | Phe |
| 1 | 3 | $CF_2$ | Cl | H | H | Phe |
| 3 | 3 | $CF_2$ | Cl | H | H | Phe |
| 1 | 3 | CHF | Cl | H | H | Phe |
| 3 | 3 | CHF | Cl | H | H | Phe |
| 1 | 1 | $CF_2$ | F | H | H | PheF |
| 2 | 1 | $CF_2$ | F | H | H | PheF |
| 3 | 1 | $CF_2$ | F | H | H | PheF |
| 5 | 1 | $CF_2$ | F | H | H | PheF |
| 1 | 1 | CHF | F | H | H | PheF |
| 2 | 1 | CHF | F | H | H | PheF |
| 3 | 1 | CHF | F | H | H | PheF |
| 5 | 1 | CHF | F | H | H | PheF |
| 1 | 2 | $CF_2$ | F | H | H | PheF |
| 2 | 2 | $CF_2$ | F | H | H | PheF |
| 4 | 2 | $CF_2$ | F | H | H | PheF |
| 1 | 2 | CHF | F | H | H | PheF |
| 2 | 2 | CHF | F | H | H | PheF |
| 4 | 2 | CHF | F | H | H | PheF |
| 1 | 3 | $CF_2$ | F | H | H | PheF |
| 3 | 3 | $CF_2$ | F | H | H | PheF |
| 1 | 3 | CHF | F | H | H | PheF |
| 3 | 3 | CHF | F | H | H | PheF |

'—' = Single bond
Cyc = 1,4-cyclohexylene
Phe = 1,4-phenylene

EXAMPLE 5

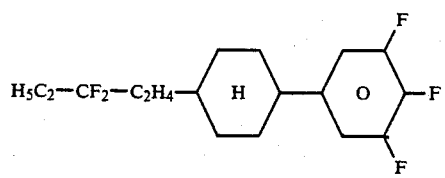

5-[trans-4-(3,3-Difluoropentyl)cyclohexyl]-1,2,3-trifluorobenzene is obtained analogously to Example 1 from 1-[trans-4-(3,4,5-trifluorophenyl)cyclohexyl]-pentan-3-one (prepared from trans-4-(3,4,5-trifluorophenyl)cyclohexanecarboxylic acid by lithium aluminum hydride reduction to the alcohol, conversion into the tosylate and malonic ester synthesis with subsequent hydrolysis and decarboxylation to give the carboxylic acid extended by two carbon atoms, conversion thereof into the nitrile and reaction with ethylmagnesium iodide).

EXAMPLE 6

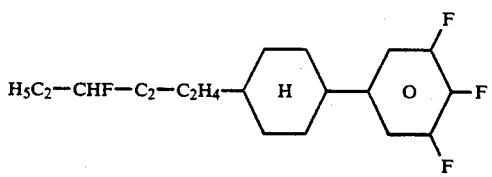

5-[trans-4-(3-Fluoropentyl)cyclohexyl]-1,2,3-trifluorobenzene is obtained analogously to Example 3 from 1-[trans-4-(3,4,5-trifluorophenyl)cyclohexyl]pentan-3-one by reduction using sodium borohydride and reaction with DAST.

The following compounds of the formula

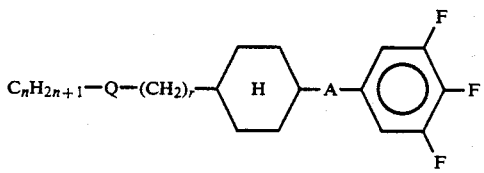

according to the invention are obtained analogously from the corresponding starting compounds

| n | r | Q | A |
|---|---|---|---|
| 1 | 0 | $CF_2$ | '—' |
| 3 | 0 | $CF_2$ | '—' |
| 5 | 0 | $CF_2$ | '—' |
| 1 | 0 | CHF | '—' |
| 3 | 0 | CHF | '—' |
| 5 | 0 | CHF | '—' |
| 1 | 1 | CHF | '—' |
| 3 | 1 | CHF | '—' |
| 5 | 1 | CHF | '—' |
| 1 | 1 | $CF_2$ | '—' |
| 3 | 1 | $CF_2$ | '—' |
| 5 | 1 | $CF_2$ | '—' |
| 1 | 2 | CHF | '—' |
| 3 | 2 | CHF | '—' |
| 5 | 2 | CHF | '—' |
| 1 | 2 | $CF_2$ | '—' |
| 3 | 2 | $CF_2$ | '—' |
| 5 | 2 | $CF_2$ | '—' |
| 1 | 1 | $CF_2$ | Cyc |
| 3 | 1 | $CF_2$ | Cyc |

-continued

| n | r | Q   | A    |
|---|---|-----|------|
| 5 | 1 | CF$_2$ | Cyc |
| 1 | 1 | CHF | Cyc  |
| 3 | 1 | CHF | Cyc  |
| 5 | 1 | CHF | Cyc  |
| 1 | 2 | CF$_2$ | Cyc |
| 3 | 2 | CF$_2$ | Cyc |
| 5 | 2 | CF$_2$ | Cyc |
| 1 | 2 | CHF | Cyc  |
| 3 | 2 | CHF | Cyc  |
| 5 | 2 | CHF | Cyc  |
| 1 | 1 | CHF | Phe  |
| 3 | 1 | CHF | Phe  |
| 5 | 1 | CHF | Phe  |
| 1 | 1 | CF$_2$ | Phe |
| 3 | 1 | CF$_2$ | Phe |
| 5 | 1 | CF$_2$ | Phe |
| 1 | 2 | CHF | Phe  |
| 3 | 2 | CHF | Phe  |
| 5 | 2 | CHF | Phe  |
| 1 | 2 | CF$_2$ | Phe |
| 3 | 2 | CF$_2$ | Phe |
| 5 | 2 | CF$_2$ | Phe |
| 1 | 1 | CF$_2$ | PheF |
| 3 | 1 | CF$_2$ | PheF |
| 5 | 1 | CF$_2$ | PheF |
| 1 | 1 | CHF | PheF |
| 3 | 1 | CHF | PheF |
| 5 | 1 | CHF | PheF |
| 1 | 2 | CF$_2$ | PheF |
| 3 | 2 | CF$_2$ | PheF |
| 5 | 2 | CF$_2$ | PheF |
| 1 | 2 | CHF | PheF |
| 3 | 2 | CHF | PheF |
| 5 | 2 | CHF | PheF |

We claim:

1. A phenylcyclohexane of formula I

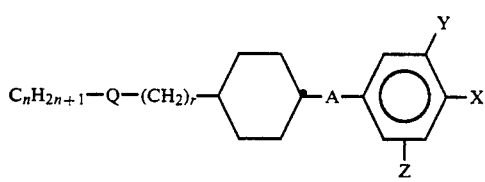

wherein
Q is CH—Hal or C—Hal$_2$;
Hal is F or Cl;
n is 1 to 5;
r is 0 to 6;
A is a single bond,

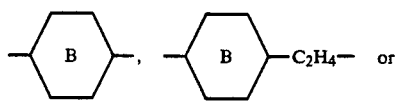

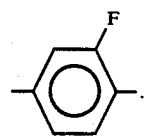

X is F or Cl; and
Y and Z are each, independently of one another, H or F.

2. In a liquid-crystalline medium containing at least two liquid-crystalline components, the improvement wherein at least one component is a phenylcyclohexane compound according to claim 1.

3. In an electrooptical display device comprising a liquid-crystal cell, the improvement wherein said liquid-crystal cell contains a medium according to claim 2.

4. In a method of generating an electrooptical display using an electrooptical display device, the improvement wherein said device is a device of claim 3.

5. A compound according to claim 1, wherein Y is F and Z is H.

6. A compound according to claim 1, wherein Y is F and Z is F.

7. A compound according to claim 1, wherein —(CH$_2$)$_r$— is a single bond, methylene, ethylene, n-propylene, n-butylene, n-pentylene, or n-hexylene.

8. A compound according to claim 1, wherein C$_n$H$_{2n+1}$ is a straight-chain alkyl having up to 3 carbon atoms.

9. A liquid-crystalline medium according to claim 3, wherein said medium contains 1%–40% of said phenylcyclohexane compound.

10. A liquid-crystalline medium according to claim 3, wherein said medium contains 3–5 phenylcyclohexane compounds of formula I.

11. A compound according to claim 1, wherein Q is —CHF— or —CF$_2$—.

12. A compound according to claim 1, wherein r is 1–3 and n is 1–5.

13. A compound according to claim 1, wherein a is a single bond, 1,4-cyclohexylene, 1,4-phenylene, or

* * * * *